United States Patent
Watanabe et al.

(10) Patent No.: US 9,427,145 B2
(45) Date of Patent: Aug. 30, 2016

(54) OPHTHALMOLOGIC MEASUREMENT APPARATUS, METHOD AND PROGRAM OF CONTROLLING THE SAME

(71) Applicant: CANON KABUSHIKI KAISHA, Tokyo (JP)

(72) Inventors: Kazuhiro Watanabe, Tokyo (JP); Sakiko Yamaguchi, Tokyo (JP); Naofumi Sekine, Kawasaki (JP); Wataru Kaku, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/728,863

(22) Filed: Jun. 2, 2015

(65) Prior Publication Data

US 2015/0351623 A1 Dec. 10, 2015

(30) Foreign Application Priority Data

Jun. 5, 2014 (JP) .................................. 2014-116999

(51) Int. Cl.
| | | |
|---|---|---|
| *A61B 3/10* | (2006.01) | |
| *A61B 3/00* | (2006.01) | |
| *A61B 3/15* | (2006.01) | |

(52) U.S. Cl.
CPC ........... *A61B 3/0025* (2013.01); *A61B 3/0041* (2013.01); *A61B 3/0083* (2013.01); *A61B 3/152* (2013.01)

(58) Field of Classification Search
CPC ..... A61B 3/0041; A61B 3/1208; A61B 3/18
USPC ................ 351/218, 217, 216, 206, 246, 200
See application file for complete search history.

(56) References Cited

U.S. PATENT DOCUMENTS

| | | | |
|---|---|---|---|
| 5,793,468 A | 8/1998 | Shalon | |
| 7,862,173 B1 * | 1/2011 | Ellman | ................ A61B 3/1208 351/217 |
| 2010/0214532 A1 | 8/2010 | Siminou | |

FOREIGN PATENT DOCUMENTS

| | | |
|---|---|---|
| CN | 2676828 Y | 2/2005 |
| CN | 101001566 A | 7/2007 |
| CN | 202198572 U | 4/2012 |
| CN | 102753085 A | 10/2012 |
| JP | H07-246188 A | 9/1995 |
| JP | H08-256984 A | 10/1996 |

* cited by examiner

*Primary Examiner* — Hung Dang
(74) *Attorney, Agent, or Firm* — Canon USA, Inc., IP Division

(57) ABSTRACT

An ophthalmologic measurement apparatus includes a measurement unit that acquires an image of an eye to be inspected, a main unit in which the measurement unit is placed and which includes a holding part for holding the main unit with a hand, an eyepiece part having a shape asymmetric about a measurement optical axis of the measurement unit and capable of being in contact with an area around an eye to be inspected, a position detection unit that detects a position of the eyepiece part, an acquisition unit that acquires eye distinguishing information indicating whether the eye is a right eye or a left eye, and a display control unit that controls a display unit to display an image of the eye such that the image of the eye is rotated in a clockwise or counterclockwise direction based on the eye distinguishing information and a resultant image is displayed.

8 Claims, 10 Drawing Sheets

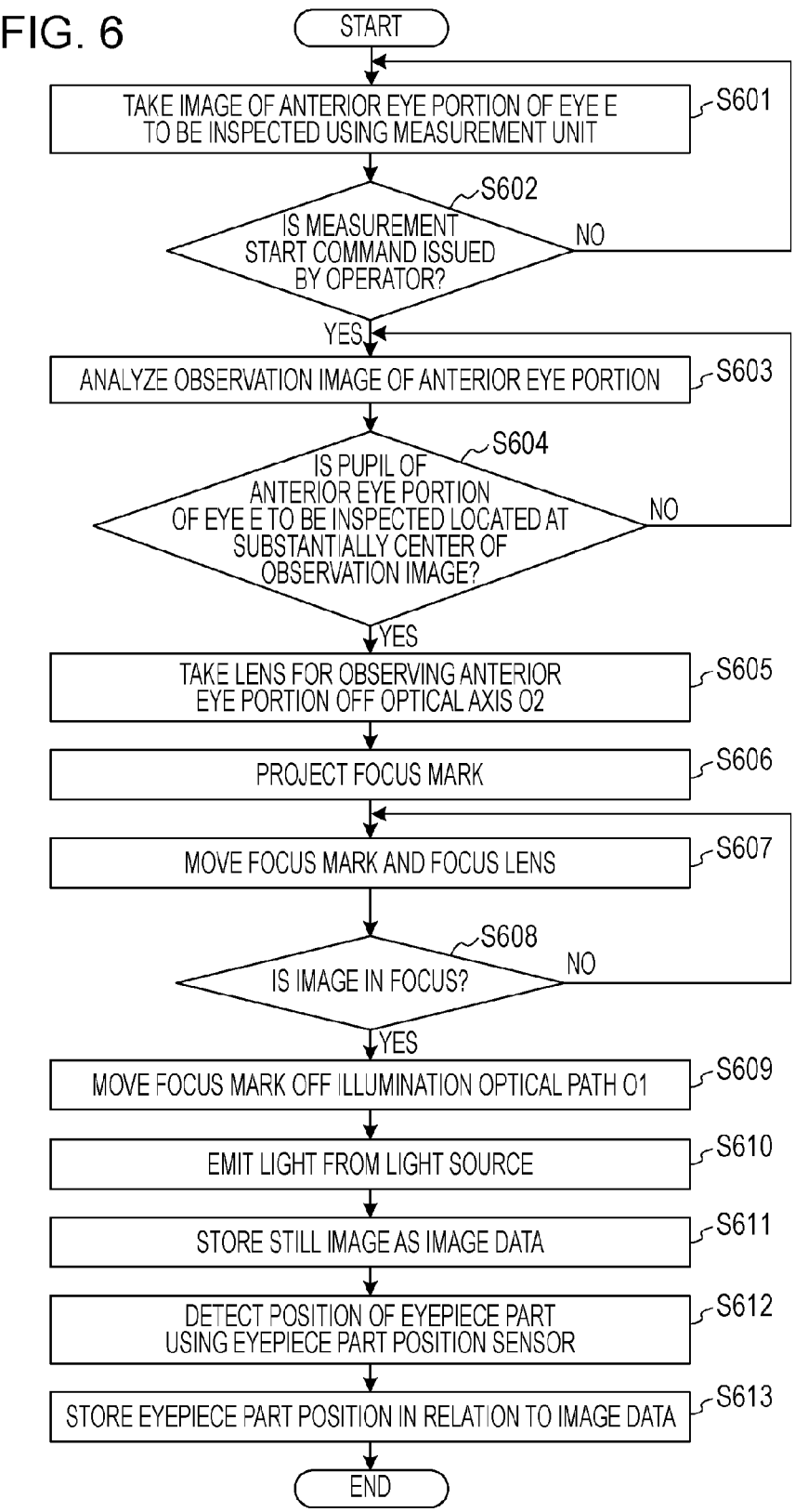

FIG. 10

| FIGURE | FIG. 9A | FIG. 9B | FIG. 9C | FIG. 9D |
|---|---|---|---|---|
| POSITION OF END PART C1 WITH RESPECT TO APPARATUS | LOWER | UPPER | LOWER | UPPER |
| INFORMATION INPUT BY OPERATOR TO INDICATE WHETHER RIGHT OR LEFT EYE IS TO BE INSPECTED | RIGHT EYE | LEFT EYE | LEFT EYE | RIGHT EYE |
| ROTATIONAL DIRECTION | 90° CLOCKWISE | 90° CLOCKWISE | 90° COUNTERCLOCKWISE | 90° COUNTERCLOCKWISE |

OPHTHALMOLOGIC MEASUREMENT APPARATUS, METHOD AND PROGRAM OF CONTROLLING THE SAME

BACKGROUND OF THE INVENTION

1. Field of the Invention

The present invention relates to an ophthalmologic measurement apparatus or the like for measuring an eye to be inspected.

2. Description of the Related Art

As for an ophthalmologic measurement apparatus for measuring an eye to be inspected, two types are known: a stationary type; and a hand-held type.

An ophthalmologic measurement apparatus of the stationary type includes a stand for putting a main part of the apparatus on an installation surface, a base configured to be slidable on the stand in back-and-forth and right-and-left directions, a measurement unit connected to the base and including various kinds of optical systems and an imaging system, a jaw receiving stand/forehead support for positioning a jaw or a forehead of a person to be inspected, and the like. In the stationary-type ophthalmologic measurement apparatus, the base is slid to the right or left mainly to switch an eye to be inspected of a person between his/her right and left eyes. Thus in the stationary-type ophthalmologic measurement apparatus, it is possible to recognize which one of right and left eyes is to be inspected by detecting whether the measurement unit is located on the right or left side with respect to the center of the stand.

On the other hand, the hand-held type ophthalmologic measurement apparatus has neither a stand nor a base, and thus it may be difficult to recognize which one of right and left eyes is to be inspected in the same manner as the stationary-type ophthalmologic measurement apparatus. To handle the above situation, Japanese Patent Laid-Open NO. 7-246188 discloses ophthalmologic equipment configured to have a shielding plate movable between a position where to shield a right eye a position where to shield a left eye, and also have a switch disposed in the inside of the main part of the equipment to allow it to recognize which one of right and left eyes is to be inspected.

On the other hand, Japanese Patent Laid-Open No. 8-256984 discloses an eye examination apparatus having a function of detecting whether an eye of interest is a right or left eye. This eye examination apparatus has two illumination units that provide illumination light from both sides of an eye examination unit, and a photosensor unit disposed between the two illumination units and configured to sense two light rays that are originally emitted from the two illumination units and reflected from a face of a person to be inspected. The photosensor unit detects a light intensity for each reflected light ray and determines, based on the detected light intensity of each reflected light ray, whether the eye to be inspected is a right or left eye.

In conventional ophthalmologic measurement apparatuses, including those disclosed in Japanese Patent Laid-Open Nos. 7-246188 and 8-256984 described above, although it is possible to recognize which one of right and left eyes is to be inspected, an eyepiece part (a so-called eyecup) has the same shape regardless of whether a right or left eye is to be inspected, and thus it is difficult to achieve a good contact between the eyepiece part and a face of a person to be inspected. More specifically, a positional relationship between a part from an inner eye corner to a nose and a part from an outer eye corner to an ear is opposite between right and left eyes. In general, the length between an eye (inner corner) and a nose is shorter than the length between an eye (outer corner) and an ear. Besides, there is a difference in an angle of a face with respect to a straight-ahead eye direction. Therefore, for example, when an eyepiece part has a shape that allows the eyepiece part to be in good contact with an area around left eye, if it is tried to directly put this eyepiece part into contact with an area around right eye, a fitting error in size and/or angle may occur.

SUMMARY OF THE INVENTION

In view of the above, the present invention provides a technique that allows it to put an eyepiece part into a good contact with an area around an eye of a person to be inspected regardless of whether it is a right or left eye.

Disclosed herein is an ophthalmologic measurement apparatus including a measurement unit configured to acquire an image of an eye to be inspected, a main unit in which the measurement unit is placed and which includes a holding part for holding the main unit with a hand, an eyepiece part having a shape asymmetric about a measurement optical axis of the measurement unit and capable of being in contact with an area around an eye to be inspected, a position detection unit configured to detect a position of the eyepiece part, an acquisition unit configured to acquire eye distinguishing information indicating whether the eye to be inspected is a right eye or a left eye, and a display control unit configured to control a display unit to display an image of the eye to be inspected such that the image of the eye to be inspected is rotated in a clockwise or counterclockwise direction based on the eye distinguishing information and a resultant image is displayed.

Further features of the present invention will become apparent from the following description of exemplary embodiments with reference to the attached drawings.

BRIEF DESCRIPTION OF THE DRAWINGS

FIG. 6 is a flow chart illustrating a process associated with an ophthalmologic measurement apparatus according to a first embodiment.

FIG. 10 is a table describing relationships among a position of an eyepiece part, information input by an operator to distinguish between right and left eyes, and a rotation angle of an image.

DESCRIPTION OF THE EMBODIMENTS

Embodiments are described below with reference to drawings.

First Embodiment

Figure 1:
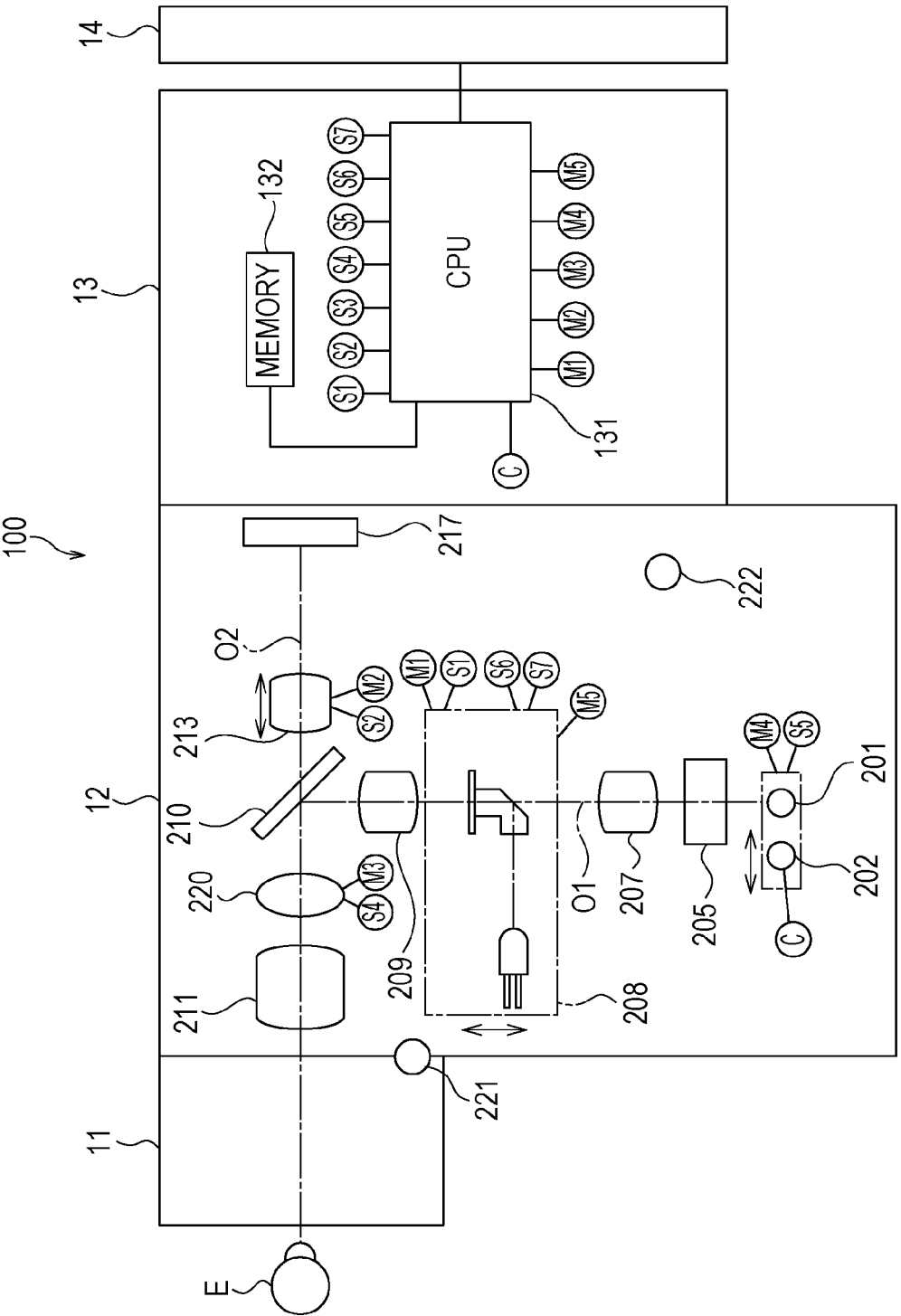
FIG. 1 is a diagram illustrating in a brief manner a structure of an ophthalmologic measurement apparatus according to an embodiment.

FIG. 1 is a diagram illustrating in a brief manner a structure of an ophthalmologic measurement apparatus 100 according to a first embodiment.

The ophthalmologic measurement apparatus 100 includes an eyepiece part 11, a measurement unit 12, a control unit 13, a display unit 14, and the like.

The eyepiece part 11 is a so-called eyecup that is to be put into contact with a face of a person to be inspected to maintain a constant distance between the measurement unit 12 and an eye E to be inspected. The eyepiece part 11 may be formed with a material having a certain degree of elasticity. The elasticity ensures that the eyepiece part 11 is put into contact with a face of a person to be inspected such that the ophthalmologic measurement apparatus 100 are easily held in a proper position and angle. Besides, the elasticity allows a reduction in pain a person to be inspected may feel when the eyepiece part 11 is put into contact with his/her face. The eyepiece part 11 may be formed with a transparent material or may have a gap. In this case, an operator is allowed to put the eyepiece part 11 into contact with a face of a person to be inspected while visually watching an eye to be inspected, which suppresses or prevents a position error between the ophthalmologic measurement apparatus 100 and the eye to be examined. The eyepiece part 11 may be formed with a material opaque to light. In this case, it is possible to prevent an eye to be inspected from being exposed to external light.

The measurement unit 12 includes an infrared light emitting diode (LED) light source 201, a while LED light source 202, a capacitor C, an illumination optical path O1, a measurement optical axis O2, a ring slit 205, an illumination relay lens 207, an illumination relay lens 209, a split unit 208, and a mirror 210 with a hole. The measurement unit 12 includes an objective lens 211, a focus lens 213, an image sensor 217, an anterior eye observation lens 220, an eyepiece part position sensor 221, an attitude sensor 222, and the like.

The infrared LED light source 201 is a light source for use in observing, in infrared light, an eye fundus of a person to be inspected. The while LED light source 202 is a light source for use in observing, in visible light, an eye fundus of a person to be inspected. The infrared LED light source 201 and the while LED light source 202 are capable of being moved by a driving unit M4 into a position in the illumination optical path O1.

The ring slit 205 is a mask for converting illumination light from the infrared LED light source 201 or the white LED light source 202 into a ring shape. The ring illumination light is focused on an eye E to be inspected via the illumination relay lens 207 and the illumination relay lens 209.

The capacitor C supplies electric power to the while LED light source 202. The amount of charge stored in the capacitor C varies depending on an image capture mode. Each time the image capture mode is changed, the capacitor C is charged and discharged properly. The charging and discharging are controlled by the control unit 13.

The split unit 208 includes a light source for use in projecting a focus target, a moving mechanism configured such that when an eye is observed, the moving mechanism enters the illumination optical path O1 and moves in either direction denoted by an up-and-down arrow to move the focus target along the optical axis, and a moving-off mechanism that moves the focus target off the illumination optical path O1 when an image is captured. The split driving motor M1 drives the split unit 208 so as to adjust the focal position of the focus target, and the split position sensor S1 detects a position at which the split unit 208 stops. The driving unit M5 moves the split unit 208 in either direction represented by an up-and-down arrow in FIG. 1, and the position sensor S6 and the position sensor S7 detect the position of the split unit 208 in the above-described situation.

The mirror with hole 210 is a total reflection mirror having a hole formed at the center thereof. The mirror with hole 210 reflects the ring illumination light from a not-hole part thereof and transmits image light via the hole at the center of the mirror with hole 210. The ring illumination light reflected by the mirror with hole 210 is focused via the objective lens 211 onto the eye to be inspected E thereby illuminating the eye to be inspected E. Light reflected from the eye to be inspected E is focused at the center of the mirror with hole 210 via the objective lens 211. The measurement optical axis O2 is an optical axis extending from the eye E to be inspected to the image sensor 217.

When the anterior eye observation lens 220 is inserted in the measurement optical axis O2, it becomes possible to observe an anterior eye. On the other hand, in a state in which the anterior eye observation lens 220 is off the measurement optical axis O2, it becomes possible to observe an eye fundus. The operation of moving the anterior eye observation lens 220 in or off the measurement optical axis O2 is performed by an anterior eye observation lens driving motor M3 and an anterior eye observation lens position sensor S4 under the control of the control unit 13.

The focus lens 213 is a lens for adjusting a focus of an image light ray passing through the hole at the center of the mirror with hole 210. The focus lens 213 moves in either direction represented by a right-and-left arrow in FIG. 1. The focus lens driving motor M2 drives the focus lens 213 according to a pulse supplied from the control unit 13. A focus lens position sensor S2 detects the position of the focus lens 213.

The image sensor 217 converts image light into an electric signal. The resultant electric signal is converted to digital data by the control unit 13. In an infrared observation mode, an observation image is displayed on the display unit 14. In an image capture mode, a captured image is stored in the memory 132 or a not-illustrated storage medium. The digital data may be transmitted via a communication unit/medium.

The eyepiece part position sensor 221 is disposed on a part where the eyepiece part 11 is connected to the measurement unit 12 so as to detect a position (the rotation angle or the slide position) of the eyepiece part 11 with reference to a main unit 20 (described later) in which the measurement unit 12 is disposed. The eyepiece part position sensor 221 is an example of a position sensor unit.

The attitude sensor 222 is a three-axis attitude sensor realized by a combination of a gyroscope sensor for measuring a three-axis angular velocity and an acceleration sensor for measuring a three-axis acceleration. The attitude sensor 222 detects the attitude of the ophthalmologic measurement apparatus 100 and more particularly the direction of the measurement optical axis O2 with respect to the vertical axis in the gravitational direction. The attitude sensor 222 is an example of an attitude detection unit.

The control unit 13 controls various operations including driving operations of the driving units M1 to M5 operations of the sensors S1 to S7, a control operation based on inputting given via the user interface, an operation of processing image data, an operation of displaying a captured image on the display unit 14, and the like. The control unit 13 receives information associated with the position of the eyepiece part 11 detected by the eyepiece part position sensor 221, and information associated with the attitude of the ophthalmologic measurement apparatus 100 detected by the attitude sensor 222.

The control unit 13 includes a CPU 131 and a memory 132. The CPU 131 executes a program stored, for example, in the memory 132 to perform various the driving control operations, the detection control operations, the data processing operation, the data input/output operation, the display control operation, and the like.

As for the display unit 14, for example, a liquid crystal display may be used. The display unit 14 displays an image of an eye to be inspected under the control of the control unit 13 or displays an image of an eye examined and stored in the memory 132. Note that the display unit 14 is also capable of displaying data about a name, an age, gender, information indicating whether the eye is a right or left eye, and the like such that the information/data is superimposed on the image of the eye to be inspected or separately from the image of the eye. The display unit 14 may be configured such that a touch panel is formed on a display surface in an integral manner thereby providing a user interface that allows an operator to perform an operation or to input a command or data. The display unit 14 may be provided either integrally with the measurement unit 12 or the like or separately from the measurement unit 12 or the like.

Figure 2:
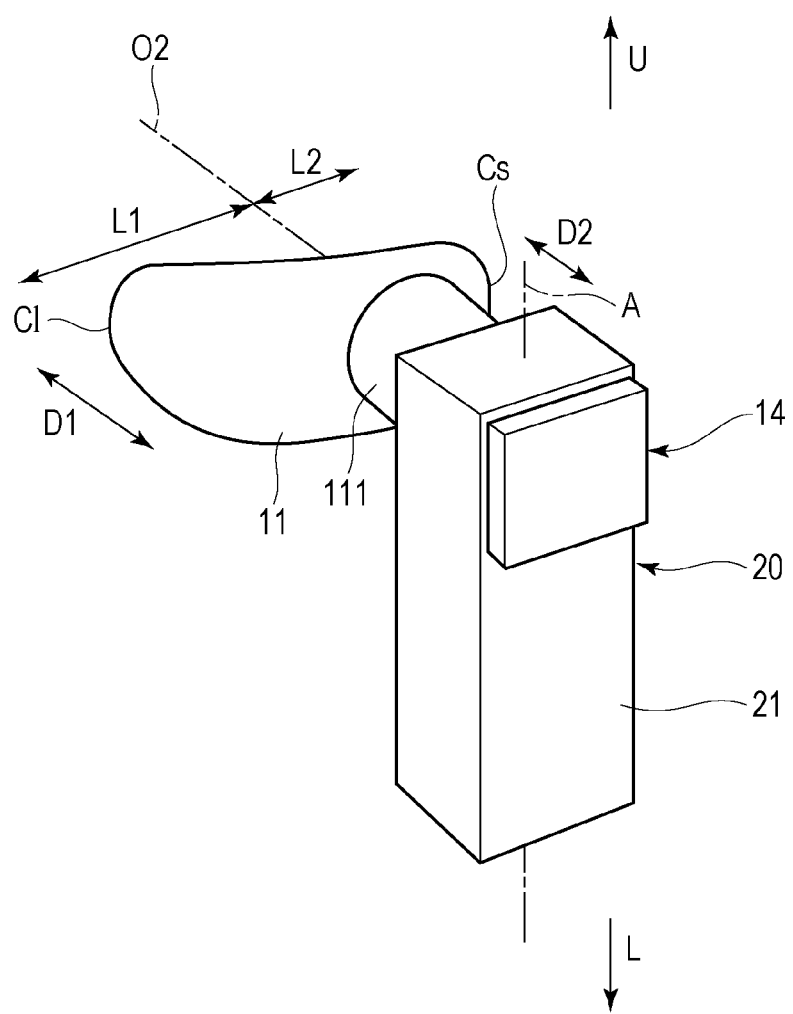
FIG. 2 is a perspective view illustrating an external appearance of an ophthalmologic measurement apparatus according to an embodiment.

FIG. 2 is a perspective view illustrating an external appearance of the ophthalmologic measurement apparatus 100 according to the present embodiment.

As illustrating in FIG. 2, the ophthalmologic measurement apparatus 100 includes, in its external structure, the eyepiece part 11, the main unit 20 in which the measurement unit 12 and the control unit 13 are disposed, and the display unit 14. In FIG. 2, O2 denotes a measurement optical axis (hereinafter also referred to as simply an optical axis O2), and A denotes a center vertical axis (hereinafter also referred to as a vertical axis A) of the main unit 20 of the ophthalmologic measurement apparatus 100.

The eyepiece part 11 is disposed on an end on one side, as seen along the optical axis O2, of the main unit 20. The eyepiece part 11 is used to put the ophthalmologic measurement apparatus 100 into contact with an eye area of a face, and more particularly, an area around an eye E to be inspected. The eyepiece part 11 is connected to the main unit 20 via a connection part 111 having a substantially cylindrical shape. In the present embodiment, the eyepiece part 11 has a substantially oval or elliptical shape whose long axis extends in a horizontal direction as seen in FIG. 2 (a direction perpendicular to the optical axis O2 and also to the vertical axis A) and is asymmetric about the optical axis O2 in the horizontal direction.

Herein, let Cl denote an end part, on one side as seen in the longitudinal direction, of the eyepiece part 11 and let Cs denote an end part on the other side, then a relation in magnitude between a distance L1 from the optical axis O2 to the end part Cl and a distance L2 from the optical axis O2 to the end part Cs is as follows: distance L1>distance L2. A relation in magnitude between a distance D1 from the main unit 20 to the end part Cl along the optical axis O2 and a distance D2 from the main unit 20 to the end part Cs along the optical axis O2 is as follows: distance D1>distance D2.

When the eyepiece part 11 is in the state illustrated in FIG. 2, it is possible to put the eyepiece part 11 into a good contact with a right eye of a person to be inspected. However, if it is tried to put the eyepiece part 11 into contact with a left eye of the person to be inspected while maintaining the state illustrated in FIG. 2, there may occur a problem that it is difficult to adjust the optical axis O2 with respect to a direction of the line of sight of the person to be inspected. In the present embodiment, to handle the above situation, an operator is allowed to select the position of the eyepiece part 11 depending on the eye to be examined is a right or left eye so as to achieve a good contact with an area around the eye. That is, the eyepiece part 11 is configured so as to be rotatable or horizontally slidable with reference to the main unit 20 such that, for example, distance L1<distance L2 and distance D1<distance D2. Referring to FIGS. 3A and 3B, FIGS. 4A to 4C, and FIGS. 5A to 5C, a description is given below as to a manner in which the eyepiece part 11 is rotated or slid.

The main unit 20 is formed in the shape of a substantially rectangular parallelepiped with its longest axis extending in a direction perpendicular to the optical axis O2. The main unit 20 includes a holding unit 21 that allows an operator to hold the ophthalmologic measurement apparatus 100 with his/her hand. The holding unit 21 is formed along an axis line of the main unit 20.

The display unit 14 is disposed on an end, on the other side as seen in the direction of the optical axis O2, of the main unit 20. The display unit 14 is formed in the shape of a substantially rectangular flat plate. The display unit 14 is disposed at a location so as to be intersected with the optical axis O2.

In FIG. 2, the ophthalmologic measurement apparatus 100 is in a position in which the display unit 14 of the main unit 20 is located on an upper side U of the ophthalmologic measurement apparatus 100 while the holding unit 21 of the main unit 20 is located on a lower side L of the ophthalmologic measurement apparatus 100.

The eyepiece part position sensor 221 is disposed at a location, not seen from the outside, that allows it to detect the position of the eyepiece part 11 and more specifically, for example, at a location where the eyepiece part 11 is connected with the main unit 20. The attitude sensor 222 is disposed at a location, not seen from the outside, inside the main unit 20.

Figure 3A:
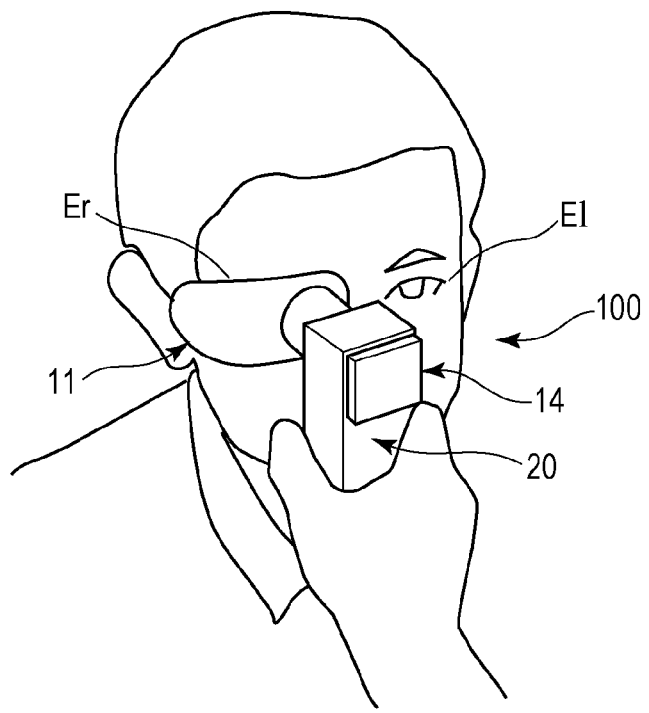
FIGS. 3A and 3B are diagrams illustrating an example of a manner in which an ophthalmologic measurement apparatus is used according to an embodiment.
Figure 3B:
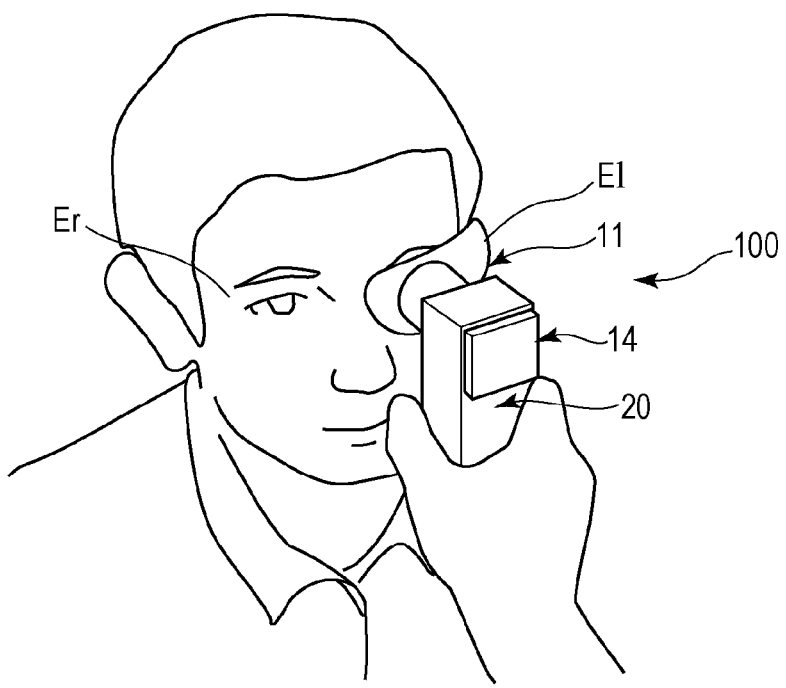

FIGS. 3A and 3B are diagrams illustrating an example of a manner in which the ophthalmologic measurement apparatus 100 is used. FIG. 3A illustrates a state in which the eyepiece part 11 is in contact with an area around a right eye (Er), and FIG. 3B illustrates a state in which the eyepiece part 11 is in contact with an area around a left eye (El). An operator is allowed to change the state of the eyepiece part 11 between a state in which the eyepiece part 11 is allowed to be in contact with an area around a right eye as illustrated in FIG. 3A and a state in which the eyepiece part 11 is allowed to be in contact with an area around a left eye as illustrated in FIG. 3B.

Figure 4A:
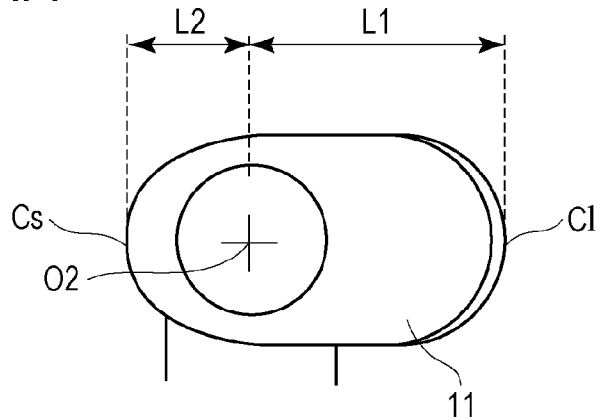
FIGS. 4A to 4c are diagrams illustrating a manner in which an eyepiece part turns.
Figure 4B:
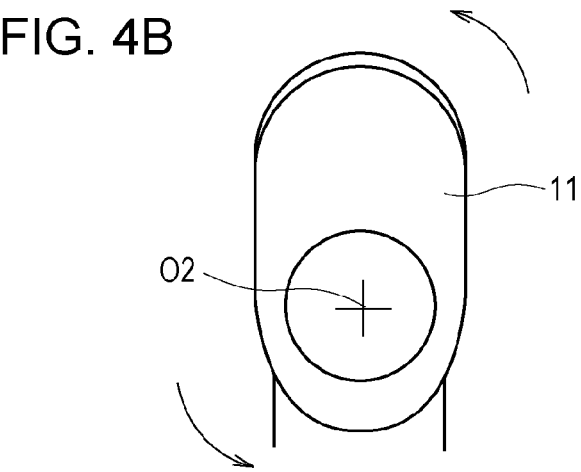
Figure 4C:
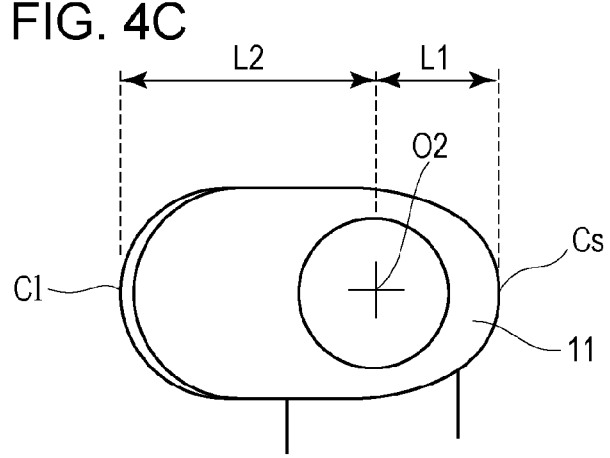

First, a structure that allows the eyepiece part 11 to turn with respect to the main unit 20 is described referring to FIGS. 4A to 4C illustrating the eyepiece part 11 seen from the side of a person to be inspected.

In FIG. 4A, the eyepiece part 11 is in a position that allows it to be contact with an area around a right eye. In this state, distance L1>distance L2. In FIG. 4B, the eyepiece part 11 is in the middle of an operation in which the eyepiece part 11 is turned about the optical axis O2 in a direction denoted by an arrow. In FIG. 4C, the eyepiece part 11 has been turned to a position that allows it to be in contact with an area around a left eye. In this state, distance L1<distance L2.

The structure that allows it to turn the eyepiece part 11 about the optical axis O2 makes it possible to put the eyepiece part 11 in a good contact with an eye regardless of whether it is a right or left eye although the eyepiece part 11 has a shape asymmetric about the optical axis O2. This makes it possible to maintain the apparatus on a face of a person to be inspected in a stable manner, and it is possible to achieve good blocking of light.

Next, a structure that allows the eyepiece part 11 to slide with respect to the main unit 20 (and more specifically, with respect to the connection part 111) is described below referring to FIGS. 5A to 5C. In each of FIGS. 5A to 5C, a view seen from the side of a person to be inspected and a view seen from the top side of the ophthalmologic measurement apparatus 100 are shown side by side.

Figure 5A:
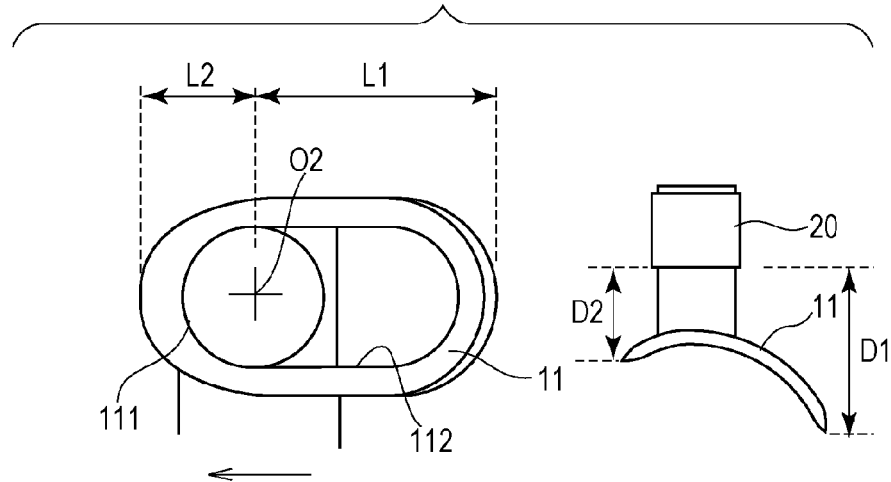
FIGS. 5A to 5C are diagrams illustrating a manner in which an eyepiece part slides.
Figure 5B:
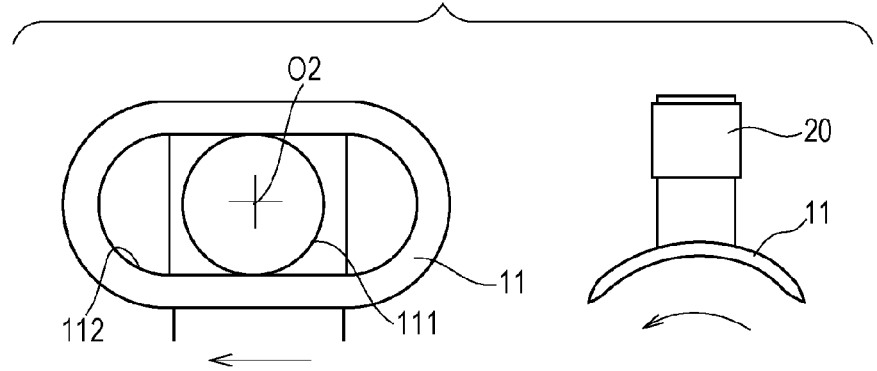
Figure 5C:
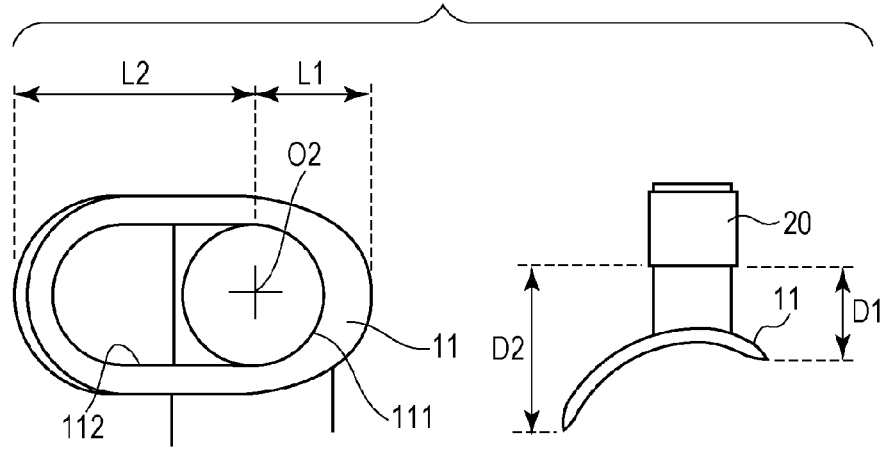

In FIG. 5A, the eyepiece part 11 is in a position in which it is allowed to be in a good contract with an area around a right eye. In this state distance L1>distance L2. In FIG. 5B, the eyepiece part 11 is in a state in which the eyepiece part 11 is being slid in a direction (horizontal direction) perpendicular to the optical axis O2 and also to the vertical axis A as denoted by arrows. In FIG. 5C, the eyepiece part 11 has been slid to a position that allows it to be in a good contact with an area around a left eye. In this state, distance L1<distance L2. As illustrated in FIG. 5A to FIG. 5C, to make it possible for the eyepiece part 11 to be slidable, the eyepiece part 11 has a long hole 112 along a direction in which the eyepiece part 11 is to be slid. By forming the eyepiece part 11 to be slidable in the horizontal direction as described above, it becomes possible to put the eyepiece part 11 in contact with either a right eye or a left eye in a good manner regardless of whether it is a right or left eye although the eyepiece part 11 has a shape asymmetric about the optical axis O2. This makes it possible to maintain the apparatus on a face of a person to be inspected in a stable manner.

The eyepiece part position sensor 221 detects the position of the eyepiece part 11, and more specifically, the rotational angle or the slide position thereof. Thus, the control unit 13 is capable of making a determination, based on the information about the position detected by the eyepiece part position sensor 221, as to whether the eyepiece part 11 is in the position that allows it to be in contact with an area around a right eye (FIG. 4A, FIG. 5A) or in the position that allows it to be in contact with an area around a left eye (FIG. 4C, FIG. 5C). That is, the control unit 13 is capable of determining whether a captured image of an eye E to be inspected is of a right eye or a left eye.

FIG. 6 is a flow chart illustrating a process perform by the control unit 13 when the ophthalmologic measurement apparatus 100 measures an eye E to be inspected according to the present embodiment. The process illustrated in this flow chart is realized by the CPU 131 in the control unit 13 by executing a program stored in the memory 132 or a storage medium.

In step S601, when an operator turns on the power of the ophthalmologic measurement apparatus 100, the control unit 13 takes an image of an eye E to be inspected via the measurement unit 12. Note that in the state immediately after the power of the ophthalmologic measurement apparatus 100 is turned on and the eyepiece part 11 is put into contact with an area around the eye E to be inspected, the anterior eye observation lens 220 is inserted in the optical axis O2.

In step S602, the control unit 13 determines whether a measurement start command is issued by an operator.

In step S603, the control unit 13 analyzes an anterior eye portion observation image.

In step S604, the control unit 13 determines whether an image of a pupil of the eye E to be inspected is located substantially at the center of the captured image. In a case where the image of the pupil of the eye E to be inspected is located substantially at the center of the captured image, the processing flow proceeds to step S605. However, in a case where the image of the pupil of the eye E to be inspected is not located substantially at the center of the captured image, the processing flow returns to step S603.

In step S605, the control unit 13 moves the anterior eye observation lens 220 off the optical axis O2.

In step S606, the control unit 13 projects a focus target.

In step S607, the control unit 13 moves the focus target and the focus lens 213.

In step S608, the control unit 13 determines whether an in-focus state is achieved or not. In a case where the in-focus state is achieved, the processing flow proceeds to step S609, but otherwise the processing flow returns to step S607.

In step S609, the control unit 13 moves the focus target off the illumination optical path O1. In step S610, the control unit 13 turns on the infrared LED light source 201 or the while LED light source 202 to emit light therefrom.

In step S611, the control unit 13 stores a still image of an eye E to be inspected as image data in the memory 132 or a storage medium.

In step S612, the control unit 13 receives information about the position of the eyepiece part 11 detected by the eyepiece part position sensor 221.

In step S613, the control unit 13 stores the information about the position of the eyepiece part 11 in relation to the image data stored in the memory 132 or the storage medium, and ends the measurement.

By storing the information about the position of the eyepiece part 11 and the image data in relation to each other as described above, it becomes possible for the control unit 13 to display on the display unit 14 image data together with information indicating the position of the eyepiece part 11. More specifically, the control unit 13 makes a determination based on the information about the position of the eyepiece part 11 as to whether the image data is of a right eye or a left eye, and displays on the display unit 14 the image data and the information indicating whether the image is of the right eye or the left eye. This makes it possible for an operator to recognize whether the stored image data is of the right eye or the left eye.

Second Embodiment

Next, in a second embodiment, a description is given for a case where a measurement is performed on an eye E of a person to be inspected in supine position.

Figure 7A:
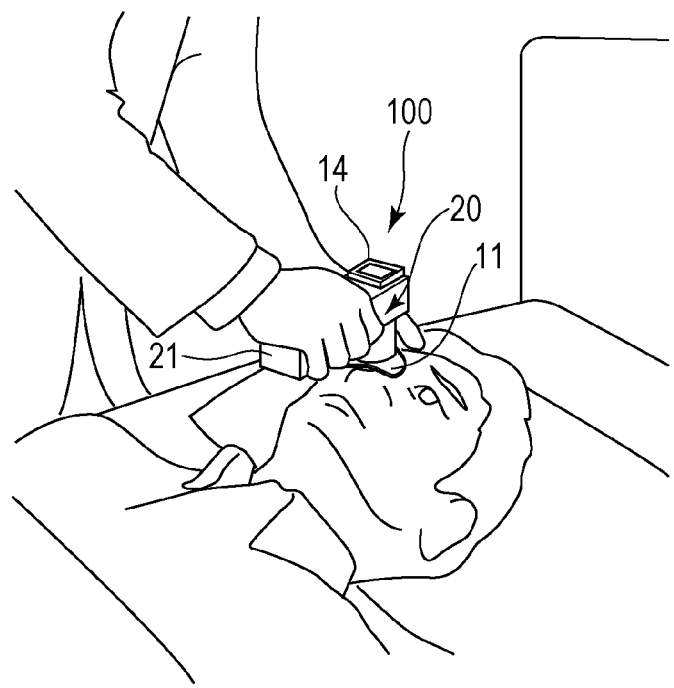
FIGS. 7A and 7B are diagrams illustrating a manner in which a measurement is performed on a person to be inspected in supine position using an ophthalmologic measurement apparatus according to an embodiment.
Figure 7B:
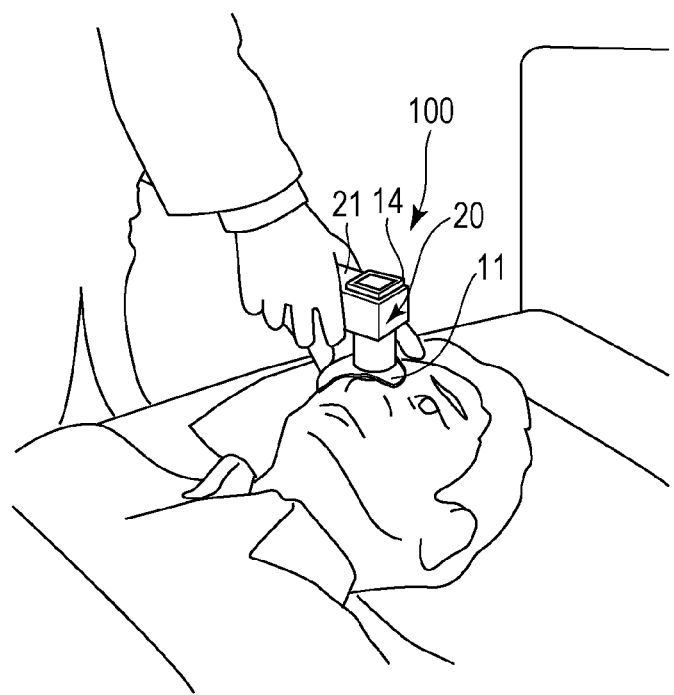

FIGS. 7A and 7B are diagrams illustrating a manner in which the ophthalmologic measurement apparatus 100 is used for a person to be inspected in supine position.

In FIG. 7A, an operator is handling the ophthalmologic measurement apparatus 100 such that the ophthalmologic measurement apparatus 100 is put in a position in which the holding unit 21 faces towards the abdomen of a person to be inspected in supine position and the eyepiece part 11 is in contact with a face of the person to be inspected. In this state, the position of the eyepiece part 11 with respect to the main unit 20 is similar to that for the case where the measurement is performed for a person to be inspected in a sitting position or a standing position. Thus the control unit 13 is capable of determining whether an eye E to be inspected is a right eye or a left eye in a similar manner to the first embodiment described above.

On the other hand, in FIG. 7B, an operator is handling the ophthalmologic measurement apparatus 100 such that the ophthalmologic measurement apparatus 100 is in a position in which the holding unit 21 faces towards a side of a person to be inspected in supine position and the eyepiece part 11 is in contact with a face of the person to be inspected. In this case, the position of the eyepiece part 11 with reference to the main unit 20 is different by about 90° in rotational position from that for the case where the measurement is performed for a person to be inspected in a sitting position or a standing position. The rotational position of the eyepiece part 11 is opposite depending on whether the eyepiece part 11 is put into contact with a person to be inspected from the right-hand side or left-hand side, and thus the rotational position of the eyepiece part 11 with reference to the main unit 20 does not indicate whether the eye E to be inspected is a right eye or a left eye.

Thus, in the present embodiment, in a case where the eyepiece part 11 is in a position in which its longitudinal direction is substantially parallel to the vertical axis A (FIG. 7B), the control unit 13 prompts an operator to input information indicating whether a right eye or a left eye is to be inspected. Furthermore, the control unit 13 displays an image of the eye E to be inspected and the like on the display unit 14 such that the image is rotated in a clockwise direction or a counterclockwise direction.

Figure 8:
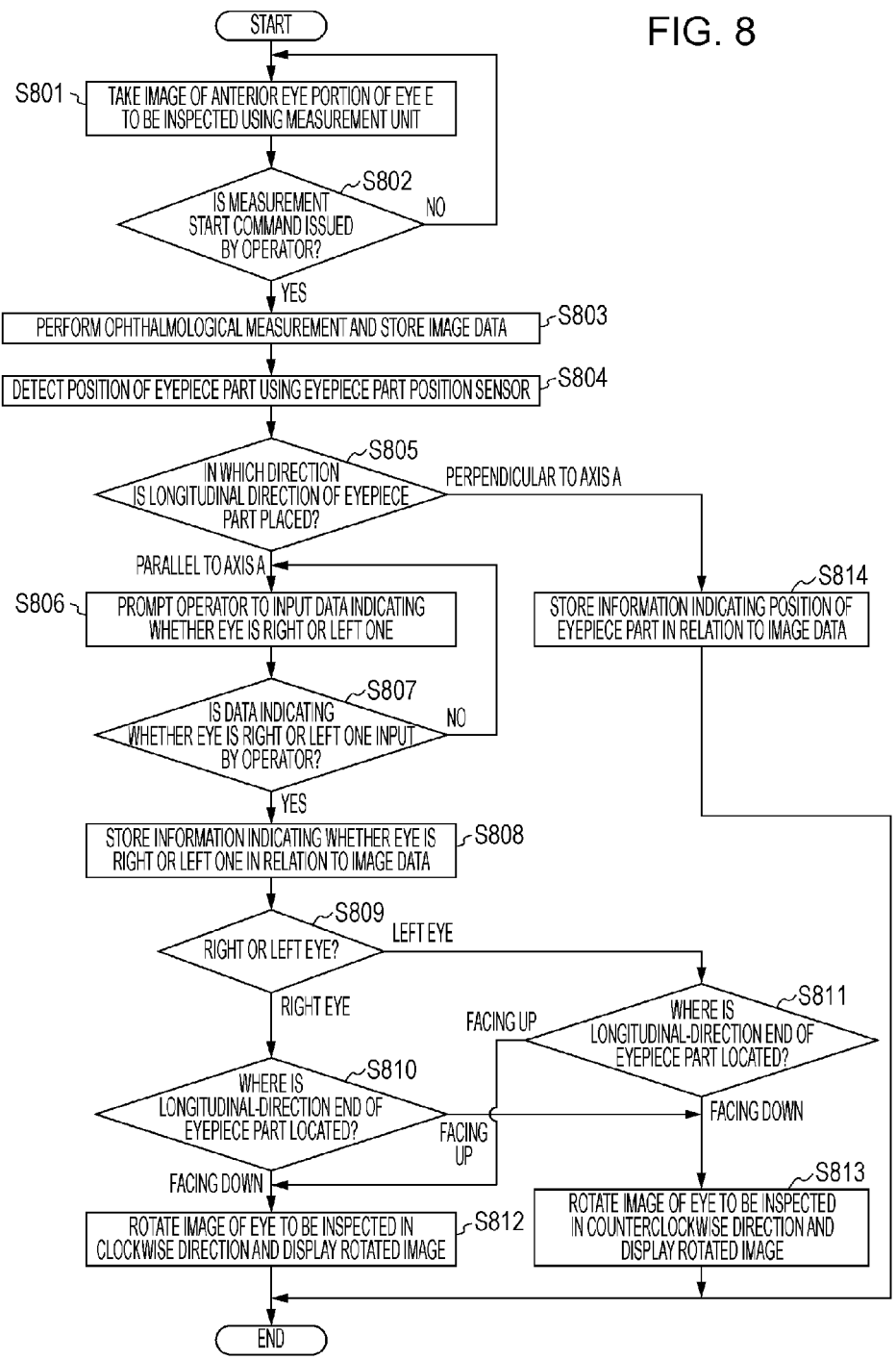
FIG. 8 is a flow chart illustrating a process associated with an ophthalmologic measurement apparatus according to a second embodiment.

FIG. 8 is a flow chart illustrating a process performed by the control unit 13 when an eye E to be inspected is measured by the ophthalmologic measurement apparatus 100 according to the present embodiment. The process illustrated in this flow chart is performed by the CPU 131 of the control unit 13 by executing a program stored in the memory 132 or another storage medium.

In step S801, when an operator turns on the power of the ophthalmologic measurement apparatus 100, the control unit 13 takes an image of an eye E to be inspected via the measurement unit 12.

In step S802, the control unit 13 determines whether a measurement start command (an image capture start command) is issued by an operator. In a case where the measurement start command is issued, the processing flow proceeds to step S803.

In step S803, the control unit 13 performs a process similar to the process from step S603 to step S611 in FIG. 6. That is, the control unit 13 performs an automatic alignment process, an automatic focusing process, and an automatic shooting process, and stores a still image of the eye E to be inspected as image data in the memory 132 or a storage medium.

In step S804, the control unit 13 receives information about the position of the eyepiece part 11 detected by the eyepiece part position sensor 221.

In step S805, based on the information about the position of the eyepiece part 11, the control unit 13 determines the direction in which the eyepiece part 11 is in. More specifically, the control unit 13 determines whether the longitudinal direction of the eyepiece part 11 is substantially parallel to or perpendicular to the vertical axis A of the main unit 20. In a case where the direction of the eyepiece part 11 is substantially parallel to the vertical axis A, the processing flow proceeds to step S806. However, in a case where the direction of the eyepiece part 11 is substantially perpendicular to the vertical axis A, the processing flow proceeds to step S814. In step S814, a process is performed in a similar manner to the process in step S613 according to the first embodiment, and the measurement is ended.

On the other hand, in step S806, the control unit 13 prompts an operator to input information indicating whether the measurement is performed for a right eye or a left eye. More specifically, the control unit 13 displays a message such as "Input information indicating which one of right and left eyes is to be inspected" on the display unit 14 thereby prompting the operator to perform inputting to indicate whether the eye is a right eye or a left eye.

In step S807, the control unit 13 waits for the operator to perform inputting via a user interface to indicate whether the eye is a right eye or a left eye. For example, the operator operates a touch panel of the display unit 14 to perform inputting to indicate that the eye is a right eye or a left eye. Thus the CPC 131 acquires via the touch panel eye distinguishing information indicating that the eye is a right eye or a left eye. In a case where inputting is performed, the processing flow proceeds to step S808.

In step S808, the control unit 13 stores the input information indicating whether the eye is a right or left eye in relation to the image data stored in the memory 132 or the storage medium.

In step S809, the control unit 13 determines whether the input information indicates a right eye or a left eye. In a case where a right eye is indicated, the processing flow proceeds to step S810. However, in a case where a left eye is indicated, the processing flow proceeds to step S811.

In step S810, the control unit 13 determines, based on the detection made by the eyepiece part position sensor 221, whether the position of the end part Cl in the longitudinal direction of the eyepiece part 11 with reference to the main unit 20 is at the upper or lower side of the ophthalmologic measurement apparatus 100. Note that the end part Cl of the eyepiece part 11 being at the upper side refers to a state in which the end part Cl of the eyepiece part 11 is located at the side of the display unit 14, while the end part Cl of the eyepiece part 11 being the lower side refers to a state in which the end part Cl of the eyepiece part 11 is located at the side of the holding unit 21 of the main unit 20. In a case where the position is lower side, the processing flow proceeds to step S812, while in a case where the position is the upper side, the processing flow proceeds to step S813.

Also in step S811, the control unit 13 determines, based on the detection made by the eyepiece part position sensor 221, whether the position of the end part Cl in the longitudinal direction of the eyepiece part 11 with reference to the main unit 20 is at the upper or lower side of the ophthalmologic measurement apparatus 100. In a case where the position is on the upper side, the processing flow proceeds to step S812, while in a case where the position is on the lower side, the processing flow proceeds to step S813.

In step S812, the control unit 13 (display control unit) rotates the image of the eye E to be inspected by 90° in the clockwise direction and displays the resultant image on the display unit 14.

On the other hand, in step S813, the control unit 13 (display control unit) rotates the image of the eye E to be inspected by 90° in the counterclockwise direction and displays the resultant image on the display unit 14.

Note that in the process of observing the eye E to be inspected, the control unit 13 may directly display the image of the eye E to be inspected on the display unit 14 without rotating the image. For example, in the observation mode (in the moving image observation mode), the control unit 13 may directly display the image of the eye E to be inspected on the display unit 14 without rotating the image, but in the image capturing mode, the control unit 13 may display the still image of the eye E to be inspected on the display unit 14 such that the image is rotated in a proper direction.

FIGS. 9A to 9D illustrate a manner in which an operator performs a measurement from a side of a person to be inspected (FIG. 7B).

Figure 9A:
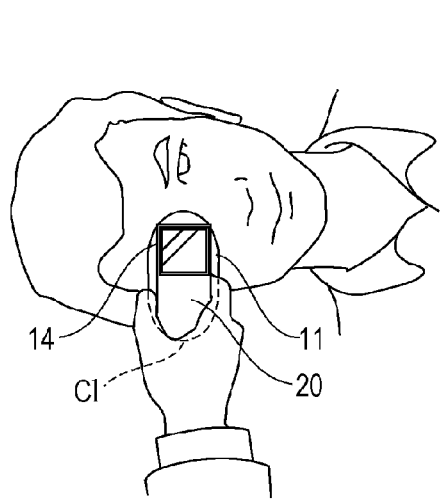
FIGS. 9A to 9D are diagrams illustrating a manner in which a measurement is performed on a person to be inspected from a side of the person to be inspected.
Figure 9B:
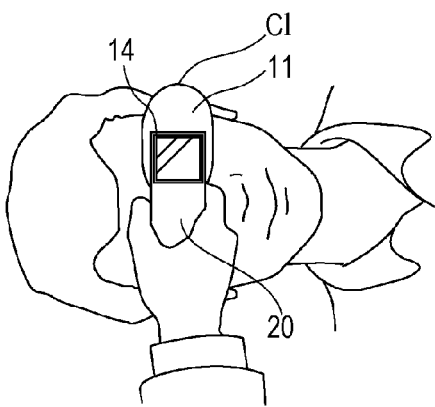

In FIGS. 9A and 9B, the measurement is performed from the right-hand side of the person to be inspected in supine position. More specifically, in FIG. 9A, the position of the end part Cl in the longitudinal direction of the eyepiece part 11 is at the lower side of the ophthalmologic measurement apparatus 100, and the operator inputs information to indicate that a right eye is to be inspected. Thus, the control unit 13 rotates the image of eye E to be inspected by 90° in the clockwise direction and displays the resultant image on the display unit 14. On the other hand, in FIG. 9B, the position of the end part Cl in the longitudinal direction of the eyepiece part 11 is at the upper side of the ophthalmologic measurement apparatus 100, and the operator inputs information to indicate that a left eye is to be inspected. Thus, the control unit 13 rotates the image of eye E to be inspected by 90° in the clockwise direction and displays the resultant image on the display unit 14.

Figure 9C:
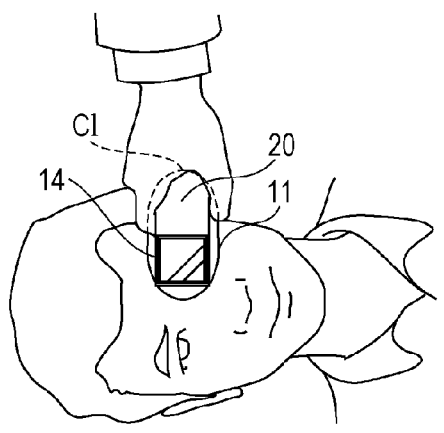
Figure 9D:
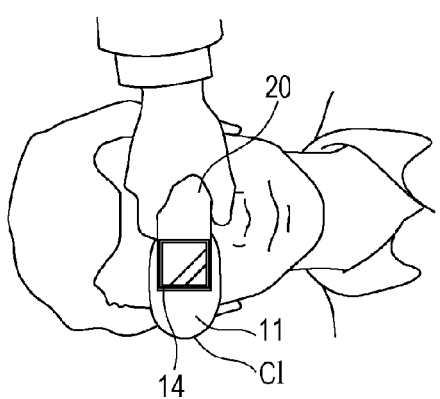

In FIGS. 9C and 9D, the measurement is performed from the left-hand side of the person to be inspected in supine position. More specifically, in FIG. 9C, the position of the end part Cl in the longitudinal direction of the eyepiece part 11 is at the lower side of the ophthalmologic measurement apparatus 100, and the operator inputs information to indicate that a left eye is to be inspected. Thus, the control unit 13 rotates the image of eye E to be inspected by 90° in the counterclockwise direction and displays the resultant image on the display unit 14. On the other hand, in FIG. 9D, the position of the end part Cl in the longitudinal direction of the eyepiece part 11 is at the upper side of the ophthalmologic measurement apparatus 100, and the operator inputs information to indicate that a right eye is to be inspected. Thus, the control unit 13 rotates the image of eye E to be inspected by 90° in the counterclockwise direction and displays the resultant image on the display unit 14.

FIG. 10 is a table illustrating correspondence among parameters in FIGS. 9A to 9D in terms of the position of the end part Cl in the longitudinal direction of the eyepiece part 11, the information input by the operator as to whether the eye to be inspected is a right or left eye, and the rotation of the image displayed on the display unit 14. Note that the correspondence table such as that illustrated in FIG. 10 is stored in the memory 132 or a storage medium such that the control unit 13 is allowed to refer to this correspondence table to determine the rotational direction of the image of the eye E to be inspected.

By displaying the rotated image on the display unit 14, it becomes possible to present the image of the eye to be inspected such that the image is in a normal position as seen from the operator even in the case where the person to be inspected in supine position is measured from a side of the person to be inspected.

Note that in the case where the control unit 13 detects via the eyepiece part position sensor 221 that the position of the end part Cl in the longitudinal direction of the eyepiece part 11 is on the upper or lower side of the ophthalmologic measurement apparatus 100, the control unit 13 may store information indicating that the image data is for a person to be inspected in supine position.

The control unit 13 is capable of detecting, via the attitude sensor 222, the attitude of the ophthalmologic measurement apparatus 100. That is, when the control unit 13 detects, via the attitude sensor 222, that the vertical axis A of the main unit 20 is substantially perpendicular to the vertical axis in the gravitational direction, or the optical axis O2 is substantially parallel to the vertical axis in the gravitational direction, the control unit 13 determines that the measurement is performed for a person to be inspected in supine position. Thus, by detecting the attitude of the ophthalmologic measurement apparatus 100 using the attitude sensor 222, the control unit 13 is capable of storing the image data in relation to information indicating that the image is that taken for a person to be inspected in supine position. Note that even in the case where the ophthalmologic measurement apparatus 100 is in the position in which the holding unit 21 faces toward the abdomen of the person to be inspected in supine position, it may be allowed to store information indicating that the image is taken for the person to be inspected in supine position.

By storing image data together with information indicating that the image data is that taken for a person to be inspected in supine position as described above, it becomes possible for the control unit 13 to display on the display unit 14 image data together with information indicating that the image data is that taken for a person to be inspected in supine position. This makes it possible for an operator to recognize that the stored image data is that taken for the person to be inspected in supine position.

According to the present embodiment, as described above, the eyepiece part 11 is configured so as to be allowed to be in contact with an area around of either a right eye or a left eye of an eye E to be inspected selected by an operator in a manner that a good contact is achieved regardless of whether the eye is a right eye or a left eye. This makes it possible to maintain the apparatus on a face of a person to be inspected in a stable manner.

Furthermore, it is possible to easily change the position of the eyepiece part 11 simply by rotating or sliding the eyepiece part 11 with reference to the main unit 20 so as to provide the optimum position depending on whether the eye E to be inspected is a right eye or a left eye.

The memory 132 or the storage medium stores the image of the eye E to be inspected captured by the measurement unit 12 and the position of the eyepiece part 11 detected by the eyepiece part position sensor 221 such that they are related to each other. Thus, when the stored image of the eye E to be inspected is reproduced, the information about the position of the eyepiece part 11 allows an operator to recognize whether the reproduced image is of a right eye or a left eye.

Furthermore, the display unit 14 displays information based on the position of the eyepiece part 11 detected by the eyepiece part position sensor 221 to indicate whether the image of the eye E to be inspected is of a right eye or a left eye. This makes it possible for an operator to recognize whether the image displayed on the display unit 14 is of a right eye or a left eye.

Furthermore, there is provided a user interface that allows an operator to input information based on the position of the eyepiece part 11 detected by the eyepiece part position sensor 221 to indicate whether the eye E to be inspected is a right eye or a left eye. Thus even in the case where an image of an eye E of a person to be inspected in supine position is taken from a side of the person to be inspected, inputting of information by an operator to indicate whether the eye E to be inspected is a right eye or a left eye makes it possible to store the image of the eye E to be inspected captured by the measurement unit 12 in relation to the information indicating whether the image is of a right eye or a left eye.

Furthermore, an image of an eye E to be inspected is rotated in a clockwise or counterclockwise direction based on the position of the eyepiece part 11 detected by the eyepiece part position sensor 221 and the information input via the user interface, and the resultant image is displayed. Thus even in the case where an image of an eye E of a person to be inspected in supine position is taken from a side of the person to be inspected, it is possible to display the image of the eye E to be inspected such that the image is in a normal position as seen by the operator.

Furthermore, based on the attitude of the ophthalmologic measurement apparatus 100 detected by the attitude sensor 222, an image of an eye E to be inspected taken by the measurement unit 12 is stored in relation to information indicating that the image is taken for a person to be inspected in supine position. This makes it possible for an operator to recognize that the stored image of the eye E to be inspected is that taken for the person to be inspected in supine position.

The present invention has been described above with various embodiments. However, the invention is not limited to those embodiments, but various modifications or combinations of embodiments are possible without departing from the scope of the invention.

For example, in the embodiments described above, the eyepiece part 11 is connected to the main unit 20 via the connection part 111. Alternatively, the eyepiece part 11 may be directly connected to the main unit 20.

Instead of employing the structure that allows the eyepiece part 11 to rotate with respect to the main unit 20, a structure may be configured such that the eyepiece part 11 is allowed to rotate with respect to the connection part 111 or such that the eyepiece part 11 and the connection part 111 are formed in an integral fashion so as to be capable of rotating with respect to the main unit 20.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-116999, filed Jun. 5, 2014, which is hereby incorporated by reference herein in its entirety.

What is claimed is:

1. An ophthalmologic measurement apparatus comprising:
    a measurement unit configured to acquire an image of an eye to be inspected;
    a main unit in which the measurement unit is placed and which includes a holding part for holding the main unit with a hand;
    an eyepiece part having a shape asymmetric about a measurement optical axis of the measurement unit and capable of being in contact with an area around an eye to be inspected;
    a position detection unit configured to detect a position of the eyepiece part;
    an acquisition unit configured to acquire eye distinguishing information indicating whether the eye to be inspected is a right eye or a left eye; and
    a display control unit configured to control a display unit to display an image of the eye to be inspected such that the image of the eye to be inspected is rotated in a clockwise or counterclockwise direction based on the eye distinguishing information and the position of the eyepiece part detected by the position by the detection unit and a resultant image is displayed.

2. The ophthalmologic measurement apparatus according to claim 1, wherein the eyepiece part is rotatable or slidable with reference to the main unit.

3. The ophthalmologic measurement apparatus according to claim 1, further comprising a storage unit configured to store the image of the eye to be inspected in relation to the position of the eyepiece part detected by the position detection unit.

4. The ophthalmologic measurement apparatus according to claim 3, further comprising
    an attitude detection unit configured to detect an attitude of the ophthalmologic measurement apparatus,
    wherein the storage unit stores, based on the attitude of the ophthalmologic measurement apparatus detected by the attitude detection unit, the image of the eye to be inspected in relation to information indicating that the image of the eye to be inspected is that taken for a person to be inspected in a supine position.

5. The ophthalmologic measurement apparatus according to claim 1, wherein the display control unit displays information based on the position of the eyepiece part detected by the position detection unit so as to indicate whether the image of the eye to be inspected is of a right eye or a left eye.

6. The ophthalmologic measurement apparatus according to claim 1, wherein
    the display control unit controls, based on the position of the eyepiece part detected by the position detection unit, the display unit to display information to prompt the eye distinguishing information, and
    the acquisition unit acquires the eye distinguishing information input by an operator.

7. A method of controlling an ophthalmologic measurement apparatus, the ophthalmologic measurement apparatus comprising
    a measurement unit configured to acquire an image of an eye to be inspected;

a main unit in which the measurement unit is placed and which includes a holding part for holding the main unit with a hand; and an eyepiece part having a shape asymmetric about a measurement optical axis of the measurement unit and capable of being in contact with an area around an eye to be inspected;

the method comprising:

detecting a position of the eyepiece part;

acquiring eye distinguishing information indicating whether the eye to be inspected is a right eye or a left eye; and displaying an image of the eye to be inspected on a display unit such that the image of the eye to be inspected is rotated in a clockwise or counterclockwise direction based on the eye distinguishing information and the detected position of the eyepiece part and a resultant image is displayed.

8. A storage medium non-transitorily storing a program to be executed by a computer to control an ophthalmologic measurement apparatus, the ophthalmologic measurement apparatus comprising a measurement unit configured to acquire an image of an eye to be inspected;

a main unit in which the measurement unit is placed and which includes a holding part for holding the main unit with a hand; and an eyepiece part having a shape asymmetric about a measurement optical axis of the measurement unit and capable of being in contact with an area around an eye to be inspected;

the program comprising:

detecting a position of the eyepiece part;

acquiring eye distinguishing information indicating whether the eye to be inspected is a right eye or a left eye; and displaying an image of the eye to be inspected on a display unit such that the image of the eye to be inspected is rotated in a clockwise or counterclockwise direction based on the eye distinguishing information and the detected position of the eyepiece part and a resultant image is displayed.

* * * * *